United States Patent [19]

Khanna et al.

[11] Patent Number: 5,208,242
[45] Date of Patent: May 4, 1993

[54] 5-SUBSTITUTED-4-PHENYL-5H-IMIDAZO[4,5-C]PYRIDINE DERIVATIVES

[75] Inventors: Ish K. Khanna, Skokie; Richard M. Weier, Lake Bluff, both of Ill.

[73] Assignee: G. D. Searle & Co., Chicago, Ill.

[21] Appl. No.: 935,761

[22] Filed: Aug. 26, 1992

[51] Int. Cl.$^5$ .................... C07D 471/04; A61K 31/53
[52] U.S. Cl. ..................... 514/303; 546/118
[58] Field of Search ......................... 546/118; 514/303

[56] References Cited

U.S. PATENT DOCUMENTS

| | | | |
|---|---|---|---|
| 4,327,100 | 4/1982 | Austel et al. | 424/256 |
| 4,336,257 | 6/1982 | Baldwin et al. | 424/256 |
| 4,914,108 | 4/1990 | Khanna et al. | 546/118 |
| 4,988,707 | 1/1991 | Stealey et al. | 546/118 |
| 4,990,518 | 2/1991 | Khanna et al. | 546/118 |
| 5,019,581 | 5/1991 | Khanna et al. | 546/118 |

FOREIGN PATENT DOCUMENTS 0260613 3/1988 European Pat. Off.

*Primary Examiner*—Marianne M. Cintins
*Assistant Examiner*—John Peabody
*Attorney, Agent, or Firm*—Joy Ann Serauskas; Paul D. Matukaitis

[57] ABSTRACT

The present invention relates to a class of 5-substituted-4-phenyl-5H-imidazo[4,5-c]pyridines represented by the formula

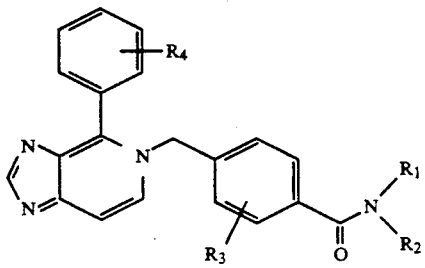

I or a pharmaceutically acceptable salt thereof useful in the treatment of diseases or disorders mediated by platelet activating factor (PAF).

10 Claims, No Drawings

5-SUBSTITUTED-4-PHENYL-5H-IMIDAZO[4,5-C]PYRIDINE DERIVATIVES

FIELD OF THE INVENTION

This invention is in the field of mammalian therapeutics and relates to compounds for treatment of mammalian diseases such as inflammation, cardiovascular disorders, asthma and other diseases. Of particular interest is a class of 5-substituted-4-phenyl-5H-imidazo[4,5-c]pyridines useful for treatment of cardiovascular and immuno-inflammatory related disorders mediated by platelet activating factor (PAF). N-Cyclohexyl-3-methoxy-N-(1-methylethyl)-4-[(4-phenyl-5H-imidazo[4,5-c]pyridin-5-yl]methyl]benzamide is a preferred embodiment of this class.

BACKGROUND OF THE INVENTION

Platelet-activating factor (PAF) has been associated with various biological activities and pathways, thus making it an important mediator responsible for a variety of physiological processes including, but not limited to, activation and aggregation of platelets, smooth muscle contraction, pathogenesis of immune complex deposition, inflammation, immunomodulation, respiratory, cardiovascular and intravascular alterations. These physiological processes are associated with a large group of diseases, such as, for example, cardiovascular disorders, asthma, lung edema, endotoxin shock, adult respiratory distress syndrome, and inflammatory diseases, autoimmunization and graft rejection.

U.S. Pat. No. 4,804,658 discloses a class of imidazopyridine derivatives useful in the treatment of diseases or disorders mediated by platelet-activating factor. The present invention is distinct from this disclosure in that in the present invention the benzamide moiety is attached to the nitrogen (position 5) which makes up the six membered ring of the imidazopyridine ring system as opposed to the disclosure wherein the benzamide moiety is attached to one of the nitrogens which makes up the five membered ring of the imidazopyridine ring system.

U.S. Pat. Nos. 4,914,108 and 5,019,581 disclose a class of imidazopyridine derivatives useful in the treatment of diseases or disorders mediated by Platelet-activating Factor. The present invention is distinct from those disclosures in that in the present invention the pyridine ring of the imidazopyridine ring system is substituted by a phenyl substituent which may be further substituted.

The present invention relates to a novel class of compounds represented by the formula

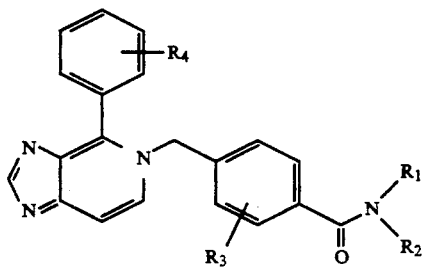

I or a pharmaceutically acceptable acid addition salt thereof, wherein $R_1$ and $R_2$ are each independently selected from the group consisting of hydrido, straight or branched chain alkyl having 1 to 6 carbon atoms or cycloalkyl having 3 to 8 carbon atoms;

$R_3$ is a group substituted at one or more of the 2, 3, 5 or 6 positions of the phenyl ring, said group being independently selected from hydrido, alkyl having 1 to 6 carbon atoms, halogen, alkoxy having 1 to 6 carbon atoms and thioalkyl wherein the alkyl has 1 to 6 carbon atoms; and $R_4$ is a group substituted at one or more of the 2, 3, 4, 5 or 6 positions of the phenyl ring, said group being independently selected from hydrido, alkyl having 1 to 6 carbon atoms, thioalkyl wherein the alkyl has 1 to 6 carbon atoms, alkoxy having 1 to 6 carbon atoms and fluoro.

The invention further relates to pharmaceutical compositions comprising a compound of formula I. Such compounds and compositions have potent and specific PAF antagonistic activities and are thereby useful in the treatment of various diseases or disorders mediated by PAF, for example inflammation, cardiovascular disorders, asthma, lung edema, and adult respiratory distress syndrome.

A preferred embodiment of the present invention is N-cyclohexyl-3-methoxy-N-(1-methylethyl)-4-[(4-phenyl-5H-imidazo4,5-c]pyridin-5-yl]methyl]benzamide which has the following structure

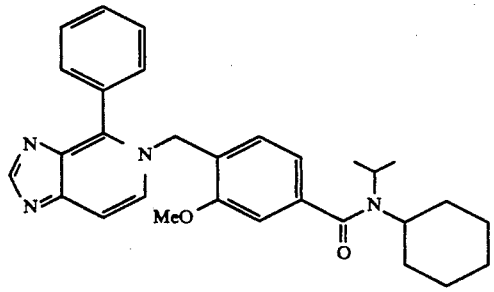

As used herein the term "alkyl having 1 to 6 carbon atoms": refers to straight chain or branched chain hydrocarbon groups having from one to six carbon atoms. Illustrative of such alkyl groups are methyl, ethyl, propyl, isopropyl, butyl, isobutyl, pentyl, neopentyl, hexyl and isohexyl.

As used herein the term "cycloalkyl having 3 to 8 carbon atoms" includes cycloalkyl groups having from 3 to 8 carbons. Illustrative of such cycloalkyl groups are cyclopropyl, cyclobutyl, cyclopentyl and cyclohexyl and 3,5-dimethylcyclohexyl.

As used herein the term halogen includes fluoro, chloro and bromo.

As used herein the term "alkoxy having 1 to 6 carbon atoms" refers to straight or branched chain ethers. Illustrative of such groups are methoxy, ethoxy, propoxy, butoxy and isopropoxy.

The term "thioalkyl" refers to straight or branched thio-containing radicals, respectively having alkyl portions of one to six attached.

Included within the embodiments of the present invention are the tautomeric forms of the described compounds, isomeric forms including geometric isomers, enantiomers and diastereoisomers, and the pharmaceutically acceptable salts thereof.

The term "pharmaceutically acceptable acid addition salt" refers to a salt prepared by contacting a compound of formula (I) with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal, infusion techniques or intraperitoneally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is selected in accordance with a variety of factors, including the type, age, weight, sex and medical condition of the patient; the severity of the infection; the route of administration; and the particular compound employed and thus may vary widely.

Dosage levels of the order from about 0.01 mg to about 100 mg per kilogram of body weight per day are useful in the treatment of the above-indicated conditions (from about 0.5 mg to about 5 gs. per patient per day). Preferably, from about 0.01 mg to about 50 mg per kilogram of body weight per daily dosage produces highly effective results (about 0.5 mg to about 2.5 gm per patient per day).

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules which may be taken singlely or multiply. These may with advantage contain an amount of active ingredient from about 0.5 to 250 mg preferably from about 0.5 to 150 mg. A suitable daily dose for a mammal may vary widely depending on the condition of the patient and other factors. However, a dose of from about 0.01 to 100 mg/kg body weight, particularly from about 0.01 to 75 mg/kg body weight may be appropriate.

The active ingredient may also be administered by injection as a composition wherein, for example, saline, dextrose or water may be used as a suitable carrier. A suitable daily dose is from about 0.01 to 100 mg/kg body weight injected per day in single or multiple doses or continuous infusion depending on the disease being treated. A preferred daily dose would be from about 0.01 to 50 mg/kg body weight.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The amount of active ingredient that may be combined with the carrier materials to produce a single dosage form which may be taken singlely or multiply will vary depending upon the host treated and the particular mode of administration. For example, a formulation intended for the oral administration of humans may contain from 0.5 mg to 250 mg of active agent compounded with an appropriate and convenient amount of carrier material which may vary from about 5 to 95 percent of the total composition. Dosage unit forms will generally contain between from about 0.5 mg to about 150 mg of active ingredient.

The compounds of Formula (I) may be prepared in accordance with the following Schemes A to C.

Scheme A
Scheme A: Generic Synthesis of 4-Substituted-1H-Imidazo[4,5-c]pyridines
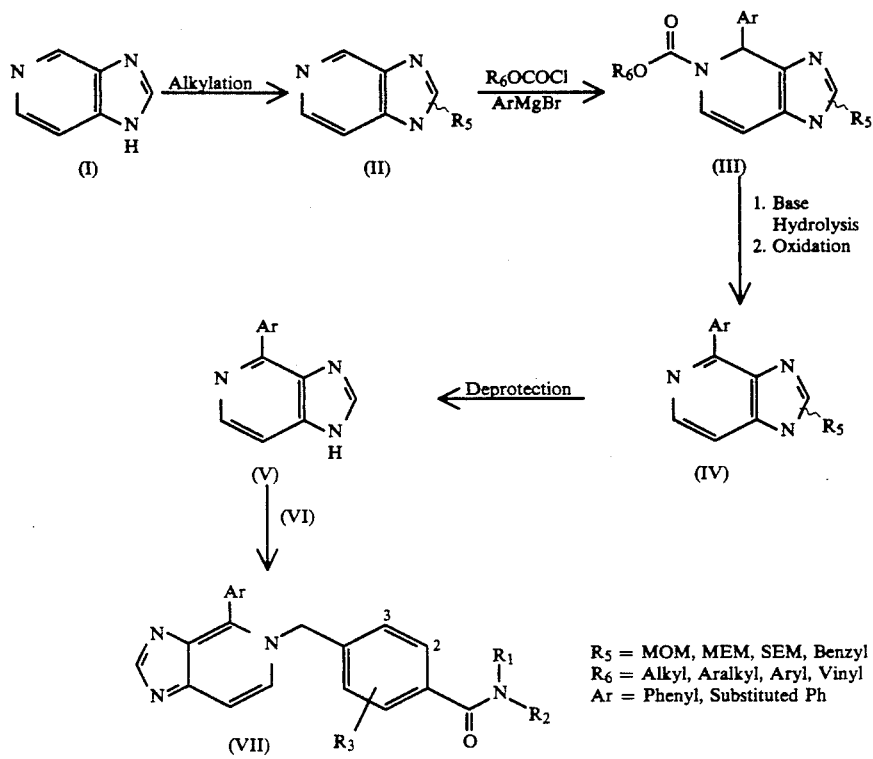
$R_5$ = MOM, MEM, SEM, Benzyl
$R_6$ = Alkyl, Aralkyl, Aryl, Vinyl
Ar = Phenyl, Substituted Ph
Scheme B
Scheme B: Synthesis of 4-Aryl-1H-Imidazo[4,5-c]pyridines
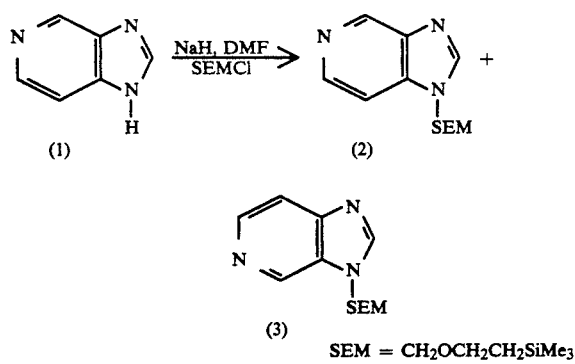
SEM = $CH_2OCH_2CH_2SiMe_3$
-continued
Scheme B
Scheme B: Synthesis of 4-Aryl-1H-Imidazo[4,5-c]pyridines
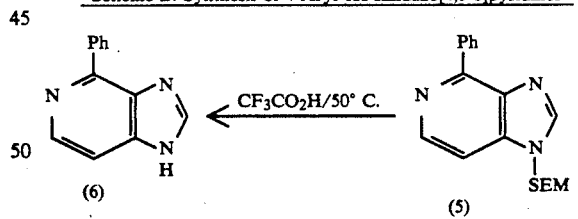
Scheme C
Scheme C: Synthesis of 4-Phenyl-1H-Imidazo[4,5-c]pyridines
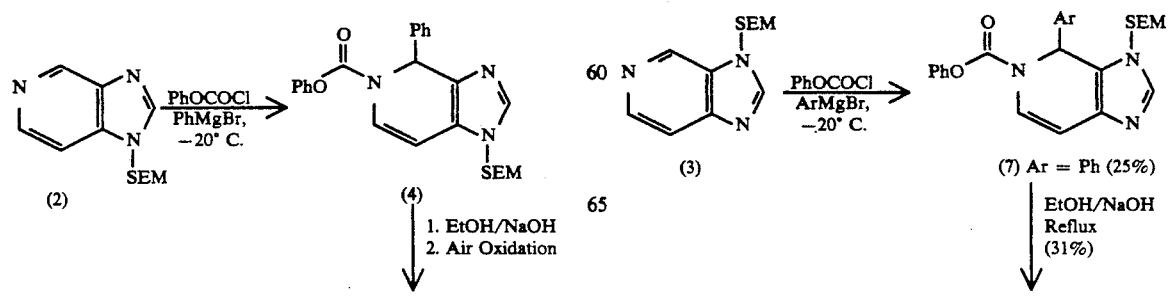

-continued
Scheme C
Scheme C: Synthesis of 4-Phenyl-1H-Imidazo[4,5-c]pyridines

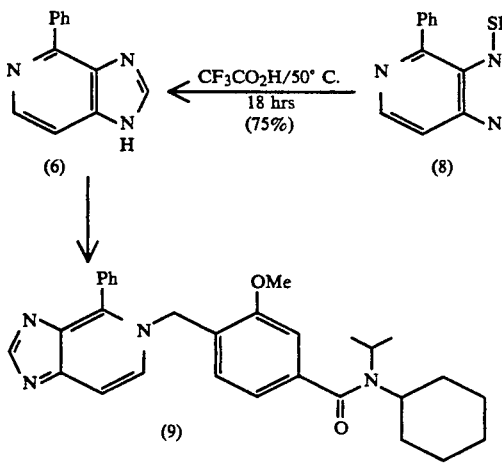

Synthesis of 5-substituted-4-aryl-imidazo [4,5-c]pyridines (VII)

These compounds can be prepared as shown in the reaction Scheme A starting with the known compound imidazo[4,5-c]pyridine. The imidazopyridine is protected at N-1 or N-3 by alkylation with alkyl halides such as 2-(trialkylsilyl)ethoxymethyl chloride, 2-methoxyethoxymethyl chloride, 2-methoxymethyl chloride or benzyl bromide in the presence of a base such as triethylamine, pyridine, potassium carbonate, cesium carbonate, sodium carbonate, sodium hydride or potassium hydride using a polar aprotic solvent such as dimethylformamide or dimethylacetamide. This reaction is carried out between 0° C. and 50° C. After chromatographic separation of the N-1 and N-3 alkylated regioisomers, the protected imidazopyrine (II) is activated by alkyl/aryl or vinyl chloroformate and reacted with arylmagnesium halides. These reactions can be carried out between −30° C. to 20° C. The suitable chloroformate reagents for this reaction are, e.g., methyl chloroformate, ethyl chloroformate, vinyl chloroformate, phenyl chloroformate, trichloroethyl chloroformate, trimethylsilylethoxy chloroformate. The 4-arylated product (III) bearing a carbamate group at position 5 is treated with aqueous base such as alcoholic (e.g., ethanolic, methanolic, isopropanolic) sodium or potassium hydroxide at 40° C. to reflux for several hours. The resulting product is oxidized either by bubbling air or using oxidizing reagents such as chloranil or DDQ to give the aromatized compound IV. The protecting group at nitrogen is then removed by judicious choice of conditions. For example, SEM (trimethylsilyl), MEM (methoxyethoxymethyl) or MOM (methyloxygenmethylene) ether may be removed by treatment with a suitable acid such as trifluoracetic acid or aqueous mineral acid such as 6N HCl. The benzyl group can be removed by, e.g., catalytic hydrogenation using Pd/C as catalyst. 4-Substituted imidazopyridine (V) is then alkylated with substituted benzyl halide (VI) with or without the presence of a base. The reaction is preferably carried out in the absence of a base using solvents such as dimethylformamide, dimethylacetamide or acetonitrile at temperatures of 20°-110° C. to give the target compound (vII).

The intermediate substituted 4-haloalkyl benzamide (VI) is prepared by following the procedures illustrated in U.S. Pat. Nos. 4,914,108 and 5,019,581.

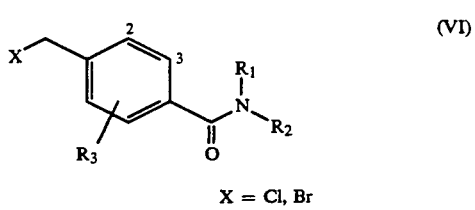

X = Cl, Br

Synthesis of 4-Substituted Imidazo[4,5-c]Pyridine Analogs

Synthesis of 1-[[2-(trimethylsilyl)ethoxy]methyl]-1H-imidazo[4,5-c]pyridine (2) and 3-[[2-(trimethylsilyl)ethoxy]methyl]-3H-imidazo[4,5-c]pyridine (3)

(Scheme B)

To a cold solution of imidazo[4,5-c]pyridine (16.5 g, 0.14 mol) in dimethylformamide (150 ml) at 0°-5° C., sodium hydride (8.3 g, 60% dispersion in mineral oil, 0.21 mol) was added in 5 portions over 30 min. After stirring at 0°-5° C. for 15 min, the reaction mixture was allowed to warm to room temperature (approx. 22° C.) and stirred for 3 hr. After recooling to −10° C., 2-(trimethylsilyl)ethoxymethyl chloride (30 ml, 0.17 mol) in dimethylformamide (50 ml) was added over 15-20 min. The cold bath was removed and the reaction was stirred for an additional 4 hr. The reaction was carefully quenched with drops of 1N HCl and the solvent removed under reduced pressure. The crude product was resuspended in methylene chloride and washed with aqueous potassium carbonate, water and brine. After drying (over MgSO4), filtration and concentration, the crude (37 g) was chromatographed (silica gel, methylene chloride/i-propanol/ammonium hydroxide (90/10/1) to give (3) (7.1 g, 20%) and (2) (12.5 g, 36%).

Compound (2) Anal calcd. for $C_{12}H_{19}N_3OSi \cdot 0.2H_2O$: C, 56.97; H, 7.73; N, 16.61. Found: C, 57.01; H, 7.62; N, 16.47, $^1H$ NMR (CDCl$_3$, ppm): 9.2 (d, J=2 Hz, 1H), 8.53 (d, J=7 Hz, 1H), 8.10 (s, 1H), 7.53 (dd, J=7, 2 Hz, 1H), 5.6 (s, 2H), 3.56 (t, J=8 Hz, 2 H), 0.95 (t, J=8 Hz, 2H), 0.4 (s, 9H).

Compound (3) Anal calcd. for $C_{12}H_{19}N_3OSi \cdot 0.75 H_2O$: C, 54.82; H, 7.86; N, 15.98. Found: C, 54.75; H, 7.99; N, 15.87, $^1H$ NMR (CDCl$_3$, ppm) 9.05 (broad s, 1H), 8.55 (d, J=7 Hz, 1H), 8.14 (s, 1H), 7.78 (dd, J=7, 2 Hz, 1H), 5.67 (s, 2H), 3.58 (t, J=8 Hz, 2H), 0.98 (t, J=8 Hz, 2H), 0.0 (s, 9H).

Synthesis of phenyl 1,4-dihydro-1-[[2-(trimethylsilyl)ethoxy]methyl]-4-phenyl-5H-imidazo[4,5-c]pyridine-5-carboxylate (Compound 4 of Scheme B)

To a cold solution (−20° C., CCl4-dry ice bath) of (2) (500 mg, 2 mmol) in THF (20 ml), phenylmagnesium bromide (0.75 ml, 3M solution in ether, 2.25 mmol) was added. A solution of phenyl chloroformate (0.26 ml, 2 mmol) in THF (5 ml) was added over 15-20 min. After stirring at −20° C. for 30 min, the cold bath was removed and the reaction stirred for 3 hr. The reaction was quenched with water and extracted with ethyl acetate. The organic layer was washed with aqueous sodium bicarbonate, water and brine. After drying (MgSO4), the solvent was removed and the crude product (880 mg) chromatographed (silica gel, hexane/ethyl acetate 6/4) to give (4) (580 mg, 65%) as colorless liquid. Anal calcd. for $C_{25}H_{29}N_3O_3Si \cdot 0.25\ H_2O$:C, 66.42; H, 6.58; N, 9.29. Found: C, 66.35; H, 6.48; N, 9.10.

Synthesis of 1-[[2-(trimethylsilyl)ethoxy]methyl]-4-phenyl-1H-imidazo[4,5-c]pyridine (Compound 5 Scheme B)

A clear solution of 4 (1 mmol) in EtOH/H$_2$O/NaOH (30/30/2) is heated at 75°–80° C. for 18 hr. After cooling, the reaction mixture is neutralized with 3N HCl and part of the solvent is removed under reduced pressure. The crude mixture is repeatedly extracted with methylene chloride and the organic layer washed with aqueous sodium bicarbonate and brine. The organic layer is dried (MgSO$_4$), concentrated and the residue is chromatographed (silica gel, methylene chloride/methanol/ammonium hydroxide 90/10/1) to give pure 5.

Synthesis of 4-phenyl-1H-imidazo[4,5-c]pyridine (Compound 6 of Scheme B) from 1-[[2-(trimethylsilyl)ethoxy]methyl]-4-phenyl-1H-imidazo[4,5-c]pyridine (Compound 5 of Scheme B)

A solution of 5 (1 mmol) in trifluoracetic acid (2 ml) is heated at 50° C. for 10 hr. The solvent is removed and the crude chromatographed on silica gel using methylene chloride/methanol/ammonium hydroxide (95/5/0.5) to give pure 6.

Synthesis of phenyl 3,4-dihydro-3-[[2-(trimethylsilyl)ethoxy]methyl]-4-phenyl-5H-imidazo[4,5-c]pyridine-5-carboxylate (Compound 7 of Scheme C)

To a cold solution (−20° C., CCl$_4$-dry ice bath) of 3 (12.6 g, 50.6 mmol) in THF (200 ml), phenylmagnesium bromide (60 ml, 3M solution in ether, 180 mmol) was added. A solution of phenyl chloroformate (6.5 ml, 50.6 mmol) in THF (50 ml) was added over 15–20 min. After stirring at −20° C. for 30 min, the cold bath was removed and the reaction stirred for 18 hr. The reaction was quenched with water and extracted with ethyl acetate. The organic layer was washed with water and brine. After drying (MgSO$_4$), the solvent was removed and the crude product (33 g) chromatographed (silica gel, hexane/ethyl acetate 6/4) to give 7 (5.5 g, 25%) as colorless liquid, $^1$H NMR (CDCl$_3$, ppm) 7.0–7.6 (complex band, 12H), 6.35, 6.38 (2s, 1H), 6.02 (d, J=8 Hz, 1H), 5.12 (d, J=11 Hz, 1H), 5.01 (d, J=11 Hz, 1H), 3.37 (m, 1H), 3.25 (m, 1H), 0.79 (m, 1H), 0.67 (m, 1H), 0.0 (s, 9H).

Synthesis of 3-[[2-(trimethylsilyl)ethoxy]methyl]-4-phenyl-3H-imidazo[4,5-c]pyridine (Compound 8 of Scheme C)

A clear solution of (7) (2.5 g, 5.59 mmol) in EtOH/H$_2$O/NaOH (60/60/4) was heated at 70° C. for 24 hr. After cooling, the reaction mixture was neutralized to pH 8 with 6N HCl and part of the solvent was removed under reduced pressure. The crude mixture was diluted with water and extracted with methylene chloride (2×400), dried (MgSO$_4$) and concentrated. The crude (2.8 g) was chromatographed (silica gel, ethyl acetate/acetone 98/2) to give (8) (558 mg, 31%), $^1$H NMR (CDCl$_3$, ppm) 8.62 (d, J=7 Hz, 1H), 8.21 (s, 1H), 7.82 (d, J=7 Hz, 1H), 7.68 (m, 2H), 7.52–7.65 (complex band, 3H), 5.28 (s, 2H), 3.2 (t, J=8 Hz, 2H), 0.81 (t, J=8 Hz, 2H), 0.0 (s, 9H).

Synthesis of 4-phenyl-1H-imidazo[4,5-c]pyridine (Compound 6 of Scheme C) from 3-[[2-(trimethylsilyl)ethoxy]methyl]-4-phenyl-3H-imidazo[4,5-c]pyridine (Compound 8 of Scheme C)

A solution of (8) (550 mg, 1.69 mmol) in trifluoroacetic acid (5 ml) was heated at 50° C. for 18 hr. The solvent was removed under reduced pressure and the crude chromatographed on silica gel using methylene chloride/methanol/ammonium hydroxide (95/5/0.5) to give (6) (245 mg, 75%), DSC (mp) 163° C. Anal calcd. for $C_{12}H_9N_3 \cdot 0.8\ H_2O$: C, 68.75; H, 5.10; N, 20.04. Found C, 68.57; H, 5.06; N, 18.98. $^1$H NMR (CD$_3$OD, ppm) 8.38 (d, J=7Hz, 1H), 8.34 (s, 1H), 8.12 (m, 1H), 7.54 (d, J=7 Hz, 1H), 7.4–7.6 (complex band, 3H).

EXAMPLE 1

Preparation of N-cyclohexyl-3-methoxy-N-(1-methylethyl)-4-[(4-phenyl-5H-imidazo[4,5-c]pyridin-5-yl)methyl]benzamide (9)

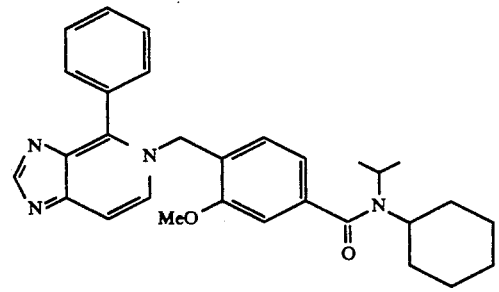

To a stirred solution of 4-phenylimidazopyridine (6) (220 mg, 1.13 mmol) in N,N-dimethylformamide (20 mL), 4-bromomethyl-3-methoxy-N-isopropyl,N-cyclohexyl benzamide (379 mg, 1.13 mmol) was added. After stirring at room temperature for 24 hr, the reaction mixture was heated at 60°–65° C. for 48 hr. The solvent was removed under reduced pressure and the crude product (720 mg) was chromatographed (silica gel, CH$_2$Cl$_2$/MeOH/NH$_4$OH 90/10/1) to give the title compound 9 (120 mg, 25%, mp 208°–10° C.) in addition to the recovered 4-phenylimidazopyridine (6) (63 mg, 29%). Anal calcd. for $C_{30}H_{34}N_4O_2 \cdot 0.6H_2O$: C, 73.02; H, 7.19; N, 11.35. Found C, 73.02; H, 7.36; N, 10.79.

EXAMPLE 2

Preparation of N-cyclopentyl-N-(3,5-dimethylcyclohexyl)-3-methoxy-4-[(4-phenyl-5H-imidazo 4,5-c]pyridin-5-yl)methyl]benzamide

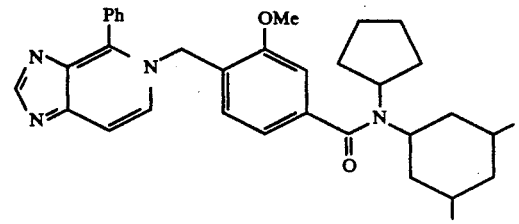

The title compound is prepared by heating a mixture of 4-phenylimidazo[4,5-c]pyridine with 4-bromomethyl-3-methoxy-N-cyclopentyl-N-3,5-dimethylcyclohexyl benzamide in dimethylacetamide at 65°-75° C. for 18 hr. After the reaction is over, the solvent is removed under reduced pressure at <50° C. and the crude product is chromatographed (silica gel, methylene chloride/methanol/ammonium hydroxide 90/10/1) to give the title compound. The intermediate 4-bromomethyl-3-methoxy-N-cyclopentyl-N-3,5-dimethylcyclohexyl benzamide is prepared following the procedure illustrated in U.S. Pat. No. 5,019,581.

EXAMPLE 3

Preparation of N-cyclopentyl-N-(3,5-dimethylcyclohexyl)-2-methoxy-4-[(4-phenyl-5H-imidazo[4,5-c]pyridin-5-yl)methyl]benzamide

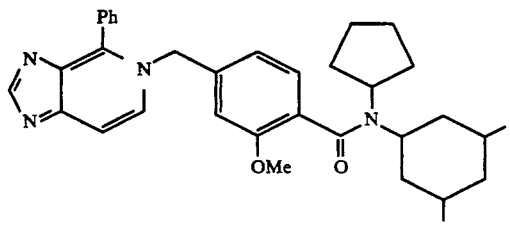

The title compound is prepared by heating a mixture of 4-phenylimidazo[4,5-c]pyridine with 4-bromomethyl-2-methoxy-N-cyclopentyl-N-3,5-dimethylcyclohexyl benzamide in dimethylacetamide at 65°-75° C. for 18 hr. After the reaction is over, the solvent is removed under reduced pressure at <50° C. and the crude product is chromatographed (silica gel, methylene chloride/methanol/ammonium hydroxide 90/10/1) to give the title compound. The intermediate 4-bromomethyl-2-methoxy-N-cyclopentyl-N-3,5-dimethylcyclohexyl benzamide is prepared following the procedure illustrated in U.S. Pat. No. 5,019,581.

EXAMPLE 4

Preparation of N-cyclobutyl-N-cyclohexyl-3-methyl-4-[(4-phenyl-5H-imidazo[4,5-c]pyridin-5-yl)methyl] benzamide

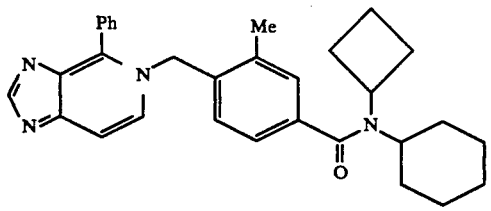

The title compound is prepared by heating a mixture of 4-phenylimidazo[4,5-c]pyridine with 4-bromomethyl-3-methyl-N-cyclobutyl-N-cyclohexyl benzamide in dimethylacetamide at 60°-75° C. for 18 hr. After the reaction is over, the solvent is removed under reduced pressure at <50° C. and the crude product is chromatographed (silica gel, methylene chloride/methanol/ammonium hydroxide 90/10/1) to give the title compound. The intermediate 4-bromomethyl-3-methyl-N-cyclobutyl-N-cyclohexyl benzamide is prepared following the procedure illustrated in U.S. Pat. No. 5,019,581.

EXAMPLE 5

Preparation of 3-bromo-N-cyclohexyl-N-cyclopentyl-4-[(4-phenyl-5H-imidazo[4,5-c]pyridin-5-yl)methyl]benzamide

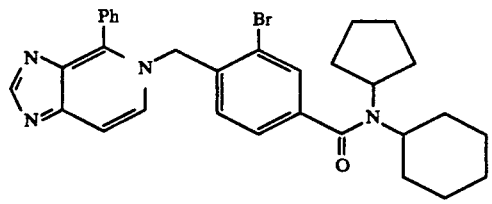

The title compound is prepared by heating a mixture of 4-phenylimidazo[4,5-c]pyridine with 4-bromomethyl-3-bromo-N-cyclopentyl-N-cyclohexyl benzamide in dimethylacetamide at 60°-75° C. for 18 hr. After the reaction is over, the solvent is removed under reduced pressure at <50° C. and the crude product is chromatographed (silica gel, methylene chloride/methanol/ammonium hydroxide 90/10/1) to give the title compound. The intermediate 4-bromomethyl-3-bromo-N-cyclopentyl-N-cyclohexyl benzamide is prepared following the procedure illustrated in U.S. Pat. No. 5,019,581.

EXAMPLE 6

Inhibition of the Specific Binding of [$^3$H]PAF to Human Platelet Membrane Preparation.

Human packed platelets were obtained from Lifesource, Inc. (Glenview, Ill.) and washed 3 times with 10 mM Trizma pH 7.0, 2 mM EDTA (dipotassium salt), 150 mM KCl and then once with 10 mM Trizma 7.4, 20 mM CaCl$_2$. The platelets were broken by freezing in a dry ice-ethanol bath, followed by thawing in 24° C. water baths. The preparation was centrifugation (40,000×g, 20 minutes, 4' C) and the pellet resuspended in 10 mM Trizma 7.4, 20 mM CaCl$_2$, 5 mg/ml human albumin. Protein concentration in the platelet membrane preparation was determined by the Lowry method [O.H. Lowry et al. *J. Biological Chemistry*, 193, 265-275 (1951)]. Aliquots of the membrane preparation were stored at −70° C. Each preparation was characterized for PAF receptor number and dissociation constant (Kd). In binding assays 5 μl of test compound, solubilized in DMSO, was added to polypropylene tubes along with 0.75 nM [$^3$H]PAF and 200 mcl [0.075 nM] of membranes and 95 μl 10 mM Trizma 7.4, 20 nM CaCl$_2$, 5 mg/ml human albumin. Tubes were incubated for 30 minutes at 24° C. The incubation was terminated by adding 4 ml of ice-cold 10 mM Trizma pH 7.4, 20 mM CaCl$_2$ and 20 mg/ml BSA prior to vacuum filtration using Whatman GF/C filters. Filters were prepared and counted for a scintillation counter. All DPM values were corrected for background and isotope decay. Triplicate determinations for single doses were averaged. The amount of non-specific binding was subtracted from all dose averages, giving an amount of specific binding in all cases. The IC$_{50}$ values were determined by the Allfit program using percent displacement data. Allfit is a 'basic' computer program for simultaneous curve fitting of a family of sigmoidal dose-response curves using the four parameter logistic equation.

The compound N-Cyclohexyl-3-methoxy-N-(1-methylethyl)-4-[(4-phenyl-5H-imidazo-[4,5-c]pyridin-5- yl]-methyl]benzamide 9 was tested in the assay described above and found to inhibit the binding of [$^3$H]-PAF to human platelet membrane with an IC$_{50}$ of 1.039 μM.

What we claim is:

1. A compound of the formula

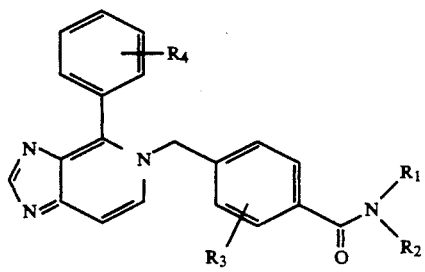

or a pharmaceutically acceptable acid addition salt thereof, wherein

R$_1$ and R$_2$ are each independently selected from the group consisting of hydro, straight or branched chain alkyl having 1 to 6 carbon atoms or cycloalkyl having 3 to 8 carbon atoms;

R$_3$ is a group substituted at one or more of the 2, 3, 5 or 6 positions of the phenyl ring said group being independently selected from hydrido, alkyl having 1 to 6 carbon atoms, halogen, alkoxy having 1 to 6 carbon atoms and thioalkyl wherein the alkyl has 1 to 6 carbon atoms; and R$_4$ is a group substituted at one or more of the 2, 3, 4, 5 or 6 positions of the phenyl ring, said group being independently selected from hydrido, alkyl having 1 to 6 carbon atoms, thioalkyl wherein the alkyl has 1 to 6 carbon atoms, alkoxy having 1 to 6 carbon atoms and fluoro.

2. A compound according to claim 1 wherein R$_3$ is alkoxy having 1 to 6 carbon atoms.

3. A compound according to claim 2 wherein the said alkoxy is methoxy.

4. A compound according to claim 1 wherein R$_1$ is isopropyl and R$_2$ is cyclohexyl.

5. A compound according to claim 1 wherein R$_4$ is hydrido.

6. A compound according to claim 1 which is N-cyclohexyl-3-methoxy-N-(1-methylethyl)-4-[(4-phenyl-5H-imidazo[4,5-c]pyridin-5-yl]methyl]benzamide.

7. A pharmaceutical composition useful for treating diseases or disorder mediated by platelet-activating factor comprising at least one compound according to claim 1, together with one or more non-toxic pharmaceutically acceptable carriers.

8. A pharmaceutical composition according to claim 7 wherein the compound is N-cyclohexyl-3-methoxy-N-(1-methylethyl)-4-[(4-phenyl-5H-imidazo[4,5-c]pyridin-5-yl]methyl]benzamide.

9. A method for treating diseases or disorder mediated by platelet-activating factor comprising administering a therapeutically effective dose of pharmaceutical composition of claim 7 to a mammal in need of such treatment.

10. A method according to claim 9 wherein the compound is N-cyclohexyl-3-methoxy-N-(1-methylethyl)-4-[(4-phenyl-5H-imidazo[4,5-c]pyridin-5-yl]methyl]-benzamide.

* * * * *

UNITED STATES PATENT AND TRADEMARK OFFICE
CERTIFICATE OF CORRECTION

PATENT NO. : 5,208,242
DATED : May 4, 1993
INVENTOR(S) : KHANNA, et al.

It is certified that error appears in the above-identified patent and that said Letters Patent is hereby corrected as shown below:

Column 2, line 25, reading "imidazo4,5-c]" should read -- imidazo[4,5-c] --.

Column 5, (4) of Scheme B reading (4)
1. EtOH/NaOH
2. Air Oxidation should read (4) (65%)
1. EtOH/NaOH
2. Air Oxidation Column 7, line 68, reading "compound (vII)." should read -- compound (VII). --.

Column 8, line 34, reading "IN HCl" should read -- 1N HCl --.

Signed and Sealed this

Thirty-first Day of May, 1994

Attest:

BRUCE LEHMAN

Attesting Officer           Commissioner of Patents and Trademarks